United States Patent [19]

Hayden et al.

[11] Patent Number: 5,099,041

[45] Date of Patent: Mar. 24, 1992

[54] PRODUCTION OF ETHYLENE OXIDE AND CATALYSTS THEREFOR

[75] Inventors: Percy Hayden, Guisbrough; Harry Pinnegar, Stockton-on-Tees, both of England

[73] Assignee: Imperial Chemical Industries PLC, London, England

[21] Appl. No.: 653,952

[22] Filed: Feb. 12, 1991

Related U.S. Application Data

[62] Division of Ser. No. 400,133, Aug. 29, 1989, Pat. No. 5,011,807.

[30] Foreign Application Priority Data

| Aug. 30, 1988 | [GB] | United Kingdom | 8820500 |
| Sep. 7, 1988 | [GB] | United Kingdom | 8820975 |
| Oct. 12, 1988 | [GB] | United Kingdom | 8823919 |
| Dec. 16, 1988 | [GB] | United Kingdom | 8829343 |

[51] Int. Cl.⁵ .................................. C07D 301/10
[52] U.S. Cl. .................................... 549/536
[58] Field of Search ........................... 549/536

[56] References Cited

U.S. PATENT DOCUMENTS

| 2,671,764 | 3/1954 | Sacken | 502/218 |
| 4,005,049 | 1/1977 | Fields | 502/317 |
| 4,007,135 | 2/1977 | Hayden et al. | 502/317 |
| 4,761,394 | 8/1988 | Lauritzen | 502/347 |
| 4,766,105 | 8/1988 | Lauritzen | 502/317 |
| 4,874,739 | 10/1989 | Boxhoorn | 502/218 |

Primary Examiner—C. Warren Ivy
Assistant Examiner—Ba K. Trinh
Attorney, Agent, or Firm—Cushman, Darby & Cushman

[57] ABSTRACT

Catalysts of attractive activities for use in the oxidation of ethylene to ethylene oxide comprise silver supported on a porous heat resisting support, a group VI A transition metal, potassium, rubidium and/or cesium and sulphur.

4 Claims, No Drawings

PRODUCTION OF ETHYLENE OXIDE AND CATALYSTS THEREFOR

This is a division of application Ser. No. 07/400,133, filed Aug. 29, 1989, now U.S. Pat. No. 5,011,807.

PRODUCTION OF ETHYLENE OXIDE AND CATALYSTS THEREFOR

This invention relates to a process for the production of ethylene oxide and catalysts therefor.

In our UK patent No. 1,491,447 catalysts for the production of alkylene oxides are described which comprise various promoters.

We have now found that a specific combination of promoters allows the production of ethylene oxide at rates much higher than those described in UK patent No. 1,491,447 and with good selectivities and catalyst lives.

This invention comprises catalysts for the production of ethylene oxide by the oxidation of ethylene with oxygen which comprise silver supported on a porous heat resisting support, a group VIA transition metal, an alkali metal selected from potassium, preferably rubidium and more preferably cesium, and sulphur, which is preferably present as sulphate ions.

It is believed that in use the sulphur content of the catalyst exists as sulphate ions.

For convenience hereafter, the term 'transition metal' will be used to mean a transition metal of Group VIA of the Periodic table, namely chromium, molybdenum or tungsten.

Silver may be introduced to a pre-formed porous heat resisting support by impregnation of the support with a solution of a silver compound, for example silver nitrate which can be reduced to silver metal if necessary by means of a reducing agent for example hydrogen. If necessary a heat treatment may be used to decompose the silver compound to silver. Suitably the impregnating solution contains a reducing agent which may be for example an anion, for example a formate, acetate, propionate, lactate, tartrate or preferably oxalate ion, of a silver compound in the solution. The reducing agent may be for example an aldehyde, for example formaldehyde or acetaldehyde or an alcohol preferably having 1 to 4 carbon atoms for example methanol or ethanol.

The solution of the silver compound may be a solution in water and/or an organic solvent, for example an aliphatic alcohol preferably having 1 to 4 carbon atoms, a polyhydric alcohol for example ethylene glycol or glycerol, a ketone for example acetone, an ether for example dioxan or tetrhydrofuran, a carboxylic acid for example acetic acid, or molten lactic acid which is preferably used in the presence of water, or an ester for example ethyl acetate or a nitrogen containing base for example pyridine or formamide or preferably an amine or diamine. An organic solvent may function as a reducing agent and/or complexing agent for the silver also.

If the silver is introduced by impregnating a support with a solution of a decomposable silver compound it is preferred that ammonia and/or a nitrogen containing base should be present. The nitrogen containing base suitably acts as a ligand maintaining the silver in solution; for example, it may be pyridine, acetonitrile, and amine, especially a primary or secondary amine having 1-6 carbon atoms, and/or preferably ammonia. Other suitable nitrogen-containing bases include acrylonitrile, hydroxylamine and alkanolamines for example ethanolamine, alkylene diamines preferably having from 2-4 carbon atoms for example vicinyl diamine or amides for example formamide or dimethyl formamide. The nitrogen-containing bases may be used alone or in admixture, mixtures of ammonia and a second nitrogen containing base or bases are used together with water. Very suitably the solution comprises silver nitrate and a lower alkyl amine having 1 to 5 carbon atoms, for example isopropylamine, in water.

The silver compound may generally be reduced to silver by heating in the range 100° C. to preferably at most 700° C. This may be carried out in the presence of an inert gas for example nitrogen or preferably an oxygen containing gas.

The transition metal, sulphur and/or alkali metal may be introduced into the catalyst before, at the same time as, or after the silver. It is preferred that at least the transition metal should be introduced at the same time as the silver. This may be achieved by impregnating the support with a solution for example as aforesaid which comprises also the transition metal and preferably also sulphate ions and the alkali metal. Sulphate ions may also be introduced as precursors, for example persulphate or sulphides which are converted in or before use of the catalyst to sulphate. If desired thioxan may be used as a complexing agent for silver in an impregnating solution. On subsequent decomposition of the silver compound to silver metal, if oxygen is present sulphate ions may be produced by oxidation of the thioxan.

The alkali metal component of the catalyst may be introduced by impregnation with a solution of an alkali metal compound, for example a sulphate, a carboxylate for example of a slat of $C_1$ to $C_{18}$ carboxylic acid, a carbonate, bicarbonate, hydroxide or nitrate. If it is introduced separately from the silver, solutions in water or preferably in solutions of lower ($C_1$ to $C_8$) alcohols or solvents with low dielectric constants (preferably below 8) may suitably be used. In the latter case, salts of $C_6$ to $C_{18}$ carboxylic acids are preferred for their solubility.

The transition metal component is suitably introduced to the catalyst as a transition metal—containing oxyanion, for example the common inorganic chromates, molybdates and tungstates especially the alkali metal and/or ammonium salts are very suitable. The transition metal sulphates may also be used.

When organic compounds with a reducing action are present there is a tendency to form organic deposits when the silver compound is decomposed. This may be marked if such compounds are amines. This tendency may be reduced by decomposing the silver compounds in the presence of oxygen for example air. Such deposits may be removed by subsequent oxidation with molecular oxygen.

If removal of organic deposits by washing is preferred it may be necessary to carry out a second impregnation to replace and if necessary supplement materials lost in the washing stage. Washing may be carried out with water and/or a $C_1$ to $C_4$ alkanol and/or $C_1$ to $C_4$ amine. The second impregnation step may be carried out using for example a solution in water or a water/alcohol mixture but is preferably carried out with a solution or colloidal solution of low dielectric constant, for example a dielectric constant of at most about 8 as measured at low frequencies at 20° C.

By 'colloidal solution' is meant a dispersion which produces a precipitation of at most 10% of the dispersed phase in the course of one day.

If desired sulphate ions may be introduced after the other component of the catalyst for example by exposing the catalyst containing the other components to $SO_3$ or other sulphur containing gas or vapour which produces sulphate ions or precursors thereof in the catalyst. For example, if sulphides are produced in the catalyst they can be oxidised to sulphate ions under the conditions of the ethylene oxide process.

If desired a pyrolysis stage may be carried out after introduction of the silver and preferably after introduction of the transition metal, alkali metal and sulphate ions also to improve the stability of the catalyst, that is, to reduce the decline in performance of the catalyst with time which it is in use. This may comprise an oxidation stage or a non oxidative heat treatment stage.

Any oxidation stage should be carried out under conditions which do not affect the silver deposit adversely; at maximum temperatures of 200° to 400° C. the residence time is not particularly critical and may be several hours but at high temperatures up to 700° C. the residence times must be short, a typical residence time at 700° C. being at most a few minutes or even seconds.

Instead of an oxidation stage, a heat treatment stage may be carried out in an inert atmosphere, for example $CO_2$ or preferably nitrogen, argon or the like. Temperatures may be used similar to those of an oxidation stage as aforesaid, but times of exposure are less critical in this case and may be for example 30 mins to 30 hours and preferably 1 to 20 hours at temperatures of 500° to 700° C. The heat treatment stage is preferably carried out after washing and either after or preferably before introducing fresh alkali metal. More than one heat treatment stage may be employed.

When the transition metal is present the temperature preferably does not exceed 550° at any time.

The transition metal and alkali metal are suitably introduced as salts, for example sulphates, salts of the transition metal oxyanions, carboxylates, or carbonates. The sulphate ions may be introduced as salts as aforesaid, amine or ammonium sulphates or sulphuric acid.

The transition metal is suitably present in the range 0.1 to 5, preferably 0.2 to 4 and more preferably 0.3 to 3 gram atoms per million grams of catalyst.

The sulphur is suitably present in the range 0.1 to 10, preferably 0.2 to 3 and more preferably 0.3 to 2 grams atoms per million grams of catalyst.

The ratio of transition metal to sulphur is suitably in the range 0.1 to 10, preferably 0.2 to 3 and more preferably 0.3 to 2.5 gram atoms per gram atom. The total of the potassium, rubidium and/or cesium component is suitably present in the range 0.1 to 15, preferably 0.2 to 12 and more preferably 0.4 to 10 gram atoms per million grams of catalyst.

The ratio of the sum of transition metal and sulphur in gram atoms to the sum of the said alkali metal component in gram atoms is suitably 0.1 to 5, preferably 0.2 to 3 and more preferably 0.3 to 2.

The transition metal is suitably present in the catalyst in the range 0.1 to 7, preferably 0.4 to 6 and more preferably 0.6 to 4 gram atoms per square kilo meter of the surface area of the support or carrier employed. One or more of the transition metals may be present.

The sulphur is suitably present in the catalyst in the range 0.1 to 14, preferably 0.4 to 4 and more preferably 0.6 to 3 gram atoms per square kilo meter of the surface area of the support. The total potassium, rubidium and/or cesium component is suitably present in the range 0.1 to 20, preferably 0.3 to 17 and more preferably 0.6 to 14 gram atoms per square kilo meter of the surface area of the support employed.

Surface areas in this specification are determined by the Brunauer, Emmet & Teller (BET) method.

Any alkali metals initially present as components of the support in non water extractable form are ignored as they do not contribute to catalysis.

If desired, in addition to the aforesaid alkali metal component sodium and/or lithium may be present. Alkaline earth metals may be present.

The porous heat resisting support preferably has a specific surface area in the range 0.05 to 10 $m^2/g$ and preferably 0.1 to 5 $m^2/g$ more preferably 0.2 to 2.5 $m^2/g$. Particularly useful are supports having a surface area of 0.3 to 1.3 $m^2/g$. The pore volume is suitably in the range 0.2 to 0.9 ml/g, preferably 0.3 to 0.8 ml/g and more preferably 0.35 to 0.6 ml/g. The support may be for example silicon carbide, zirconia or silica. Alpha-alumina is preferred.

Most of the silver content of the catalyst is preferably present in the form of discrete particles adhering to the support having equivalent diameters of less than 1,000 nm preferably in the range 2–1,000 nm and more preferably 4–800 nm. By equivalent diameter is meant the diameter of a sphere of the same silver content as the particle.

Preferably at least 80% of the silver is present as particles having equivalent diameters in the aforesaid range, the quantity of silver being judged in terms of the number of particles falling in that range. The silver may be present as silver and/or silver oxide and is thought to be present normally as silver particles having an oxidised surface layer. The dimensions of the silver particles may be determined by scanning electron microscopy.

The catalyst preferably comprises 3 to 50% and more preferably 5 to 20% by weight of silver.

The invention also comprises a process in which ethylene oxide is produced by contacting ethylene and oxygen with a catalyst according to the invention, preferably oxidising at least one and more preferably two moles of ethylene per liter of catalyst bed per hour thereby.

Partial pressures of ethylene in such processes may be in the range 0.1–30 and preferably 1 to 30 bars. The total pressure may be in the range of from 1 to 100 and preferably 3–100 bars absolute. The molar ratio of oxygen to ethylene may be in the range 0.05 to 100. The partial pressure of oxygen may be in the range 0.01 and preferably 0.1 to 20 bars and preferably 1–10 bars. The oxygen may be supplied for example in the form of air or preferably as commercial oxygen. A diluent for example helium, nitrogen, argon and/or carbon dioxide and/or preferably methane may be present in proportions of 10–80% and preferably 40–70% by volume in total. Ethane may also be present preferably in the range 0.1–5% by volume. It is necessary to operate using gas compositions which are outside the explosive limits.

The temperature is suitable in the range 200°–300° C., and preferably in the range 210°–290° C. Contact times should be sufficient to convert 0.1–70%, for example 2 to 20% and preferably 5–20% of the ethylene and unconverted ethylene is suitably recycled.

A reaction modifier is suitably present. Suitable reaction modifiers comprise chlorine and may be for example chlorinated alkenes having 1–6 carbon atoms for example methyl chloride or teriary butyl chloride, dichloromethane or chloroform, a chlorinated biphenyl or polyphenol, a chorinated benzene which may be for example monochlorobenzene or especially vinyl chloride or ethylene dichloride. The concentration of the reaction modifier depends on its chemical nature for example in the case of ethylene dichloride 0.02 to 10 and preferably 0.05-5 parts per million by weight are normally present and in the case of vinyl chloride 0.05 to 20 and preferably 0.1-10 parts by million by weight are suitably present.

We have found that with appropriate concentrations of such reaction modifiers, especially vinyl chloride, attractive selectivities may be secured.

Any small loss of sulphur and/or transition metal component from the catalyst during use may be replenished by the provision of volatile sulphur and/or transition metal compounds in gases fed to the catalyst.

EXAMPLE 1

Preparation of Catalyst

Silver oxalate of formula weight 303.8 (9.2 g) was dissolved in aqueous ethylene diamine (35% v/v ethylene diamine; 126 mls).

Ammonium chromate of formula weight 152.1 (2.92 g) was dissolved in water (50 mls).

Ammonium sulphate of formula weight 132.1 (1.03 g) was dissolved in 50% v/v aqueous ethylene diamine (50 mls).

Cesium oxalate of formula weight 371.8 (3.50 g) was dissolved in water (50 mls).

A solution comprising silver, chromium, sulphur and cesium was prepared by mixing the above mentioned silver solution (6.73 mls), the chromium solution (0.04 mls), the sulphate solution (0.18 mls) and the cesium solution (0.25 mls).

An alpha-alumina support (A) (pore volume 0.44 mls/g; surface area, 0.70 m$_2$/g, as determined by the BET method; silicon content, 2850 ppm; acid leachable sodium content, 57 ppm, (ppm in each case being parts per million by weight) acid leachable potassium content 10 ppm; shape, hollow cylinders; dimensions, 8 × 8 mms with 3 mm hole along the axis; weight 5.02 gram) was impregnated with the solution comprising silver, chromium, and cesium described above by soaking therein for 10 minutes with periodic exposure to a vacuum pump. In this way the porous volume of the support was filled with the said solution. The impregnated support was drained free of excess solution. The damp solid was placed inside a stainless steel basket which was subsequently positioned in a stream of hot air at 265° C. The basket was rotated so that the supported catalyst was exposed evenly to the flow of hot air. The hat time was five minutes during when the silver compound was reduced to silver metal.

Composition of the Catalyst

The composition of the finished catalyst (catalyst 1) expected from the filling of the support's porous volume was 1537 gram atoms of silver per million grams of catalyst, 0.8 gram atoms of chromium per million grams of catalyst, 1.5 gram atoms of sulphur per million grams of catalyst and 5.0 gram atoms of cesium per million grams of catalyst. This composition is in excess of any quantities of sodium and potassium that may be extracted from the support into the impregnating solution and re-deposited during the subsequent drying stage.

Testing the Catalyst

The catalyst was crushed and sieved to produce particulate matter in the size range 425 to 1000 microns. An aliquot (0.4 g) was loaded into a middle section of a stainless steel reactor (length, 25.4 cms; internal diameter 3 mm).

A gas mixture of ethylene (40%), oxygen (8), carbon dioxide (4.8%), vinyl chloride (1.4 ppm), ethyl chloride (0.5 ppm) with nitrogen to balance was passed at a pressure of 16 atmospheres absolute over the catalyst. The gas was passed at an hourly spaced velocity of 3600. All precentages and parts per million (ppm) of the gas mixture are by volume. The temperature of the reactor was adjusted to achieve 30% conversion of the oxygen fed: this is designated $T_{30}$.

The selectivity of the catalyst, S, is the number of moles of ethylene oxide produced expressed as a percentage of the number of mole of ethylene consumed. $S_{30}$ is the selectivity at 30% conversion of the oxygen fed. The results of testing catalyst 1 are in Table 1.

EXAMPLE 2

Catalyst 2 was made according to the procedures used in example 1 excepting that a different aliquot of the chromium solution was used to yield catalyst 2. The results of testing catalyst 2 according to the procedures of example 1 are shown in Table 1.

COMPARATIVE EXAMPLES 1 TO 3

Catalysts I, II, and II were made according to the methods described in example 1 excepting that one of the components other than silver was omitted from the catalyst precursor solution. These catalysts were tested as described in example 1 and the results are shown in Table 2.

V/v means by volume.

EXAMPLE 3

The procedure of example 1 was repeated with molybdenum as the transition metal component of the catalyst.

Silver oxalate of formula weight 303.8 (94.5 g) was dissolved in aqueous ethylene diamine (35% v/v ethylene diamine; 126 mls).

Ammonium paramolybdate of formula weight 1235.9 (1.84 g) was dissolved in 50% v/v aqueous ethylene diamine (50 mls).

Ammonium sulphate of formula weight 132.1 (1.03 g) was dissolved in 50% v/v aqueous ethylene diamine (50 mls).

Cesium oxyalate of formula weight 371.8 (3.50 g) was dissolved in water (50 mls).

A solution comprising silver, molybdenum, sulphur and cesium was prepared by mixing the above mentioned silver solution (6.73 mls), the molybdenum solution (0.12 mls), the sulphate solution (0.18 mls) and the cesium solution (0.25 mls).

An alpha-alumina support (A) was impregnated with the above solution as described in example 1.

The composition of the finished catalyst (catalyst 3) expected from the filling of the support's porous volume was 1435 gram atoms of silver per million grams of catalyst, 1.3 gram atoms of molybdenum per million grams of catalyst, 1.4 gram atoms of sulphur per million grams of catalyst and 4.8 grams atoms of cesium per million grams of catalyst.

The catalyst was tested according to the procedure of example 1 modified as follows.

A gas mixture of ethylene (44%), oxygen (8%), carbon dioxide (0.5%), vinyl chloride (1.2 ppm), ethyl chloride (0.6 ppm) with nitrogen to balance was passed at a pressure of 16 atmospheres absolute over the catalyst. The gas was passed at an hourly space velocity of 3600.

The results of testing catalyst 3 are in table 3.

EXAMPLES 4 TO 7

Catalysts 4 to 7 were made according to the procedures used in example 3 excepting that different aliquots of the silver, molybdenum, sulphur and cesium solutions were mixed together to provide a series of solutions containing approximately the same amounts of silver, sulphur and cesium but differing levels of molybdenum to yield catalysts 4 to 7. The results of testing these catalysts as in example 3 are shown in Table 3.

EXAMPLE 8

Catalyst 3 was also tested as in example 3 but with a gas hourly space velocity of 7200. The results are shown in Table 4.

EXAMPLE 9 TO 12

Catalysts 8 to 11 were made in a manner similar to catalyst 3 but with differing proportions of ammonium sulphate solution relative to each other. The catalysts were tested as in example 3 and the results are shown in Table 4.

EXAMPLE 13

Catalyst 12 was prepared on a second alpha-alumina support (B) (pore volume, 0.37 ml/g; surface area, determined by the BET method, 0.65 m$^2$/g; silicon content, 1073 ppm; leachable sodium content, 30 ppm; leachable potassium content, 8 ppm; shape, hollow cylinders, dimensions 8×8 mms with 3 mm hole along the axis) using the method described in example 3. Appropriate volumes of the solution of silver, molybdenum, sulphate and cesium were mixed to yield a catalyst having the expected composition set out for catalyst 12 in Table 4. The catalyst was tested as described in example 3 and the results are shown in table 4.

EXAMPLE 14 AND 15

Catalyst 3 and 5 were tested as in example 3 excepting that the CO$_2$ level in the feed gas was 5% v/v. The results are shown in Table 5.

EXAMPLE 16

Catalysts 13 was made using the procedure in example 3 excepting that the catalyst composition, calculated from the composition of the impregnating solution and the pore volume of support A, was 1450 gram atoms of silver, 2 gram atoms of molybdenum, 1 gram atom of sulphur and 4.8 gram atoms of cesium all per million grams of catalyst. Catalyst 13 was tested as in example 3. S$_{30}$ was 85% and T$_{30}$ was 235° C.

EXAMPLE 17

Catalyst 14 was made to the composition of catalyst 8 excepting that 0.5 mole of lithium sulphate and 1 mole of sodium sulphate, each per million grams of catalyst, were also included. Thus the total alkali metal content of catalyst 14 was expected to be 7.8 gram atoms per million grams of catalyst and the total sulphur content was expected to be 2.5 gram atoms per million grams of catalyst. Catalyst 14 was tested as in Example 3. S$_{30}$ was 84.3% and T$_{30}$ was 239° C.

COMPARATIVE EXAMPLES 4 TO 11

Catalyst IV and XI were made according to the methods set out in example 3 excepting that one or two of the components other than silver were omitted from the catalyst precursor solution. These catalysts were tested as described in example 3 and the results are shown in Table 6.

EXAMPLE 18

The procedure of example 1 were repeated with tungsten as the transition metal component of the catalyst.

Silver oxalate of formula weight 303.8 (94.5 g) was dissolved in aqueous ethylene diamine (35% v/v ethylene diamine; 126 mls).

Ammonium tunstate of formula weight 283.9 (1.54 g) was dissolved in 20% v/v aqueous ethylene diamine (50 mls).

Ammonium sulphate to formula weight 132.1 (1.03 g) was dissolved in 50% v/v aqueous ethylene diamine (50 mls).

Cesium oxalate of formula weight 371.8 (3.50 g) was dissolved in water (50 mls).

A solution comprising silver, tungsten, sulphur and cesium was prepared by mixing the above mentioned silver solution (7.9 mls), the tungsten solution (0.32 mls), the sulphate solution (0.19 mls) and the cesium solution (0.28 mls).

An alpha-alumina support (A) was impregnated with the above solution as described in example 1.

The composition of the finished catalyst (catalyst 15) expected from the filling of the support's porous volume was 1405 gram atoms of silver per million grams of catalyst, 1.7 gram atoms of tungsten per million grams of catalyst, 1.4 gram atoms of sulphur per million grams of catalyst and 5.1 gram atoms of cesium per million grams of catalyst.

The catalyst was tested according to the procedure of example 1 as follows.

A gas mixture of ethylene (50%), oxygen (8%), carbon dioxide (0.5%), vinyl chloride (1.5 ppm), ethyl chloride (0.7 ppm) with nitrogen to balance was passed at a pressure of 16 atmospheres absolute over the catalyst. The gas was passed at an hourly space velocity of 3600.

The results of testing catalyst 15 are in table 7.

EXAMPLES 19 AND 20

Catalyst 16 and 17 were made according to the procedures used in example 18 excepting that different aliquots of the silver, tungsten, sulphur and cesium solutions were mixed together to provide two solutions containing approximately the same amounts of silver and sulphur but differing levels of tungsten and cesium to yield catalysts 16 and 17. The results of testing these catalysts as in example 18 are shown in Table 7.

EXAMPLES 21 AND 22

Catalysts 15 and 16 were tested as in example 18 excepting that the CO$_2$ level in the feed gas was 5% v/v. The results are shown in Table 7.

EXAMPLE 23

Catalyst 18 was prepared in the same manner as catalyst 3 excepting that the molybdate, sulphate and cesium solutions were made up such that a volume equivalent to the pore volume of the catalyst provided 0.9 g atoms of molybdenum, 2.3 g atoms of sulphur, and 6.3 g atoms of cesium per million g of catalyst. In tests according to the procedure of example 3 $S_{30}$ was 85.3%, $T_{30}$ was 228° C. and the rate of ethylene oxidation was 4.2 moles/liter hour.

EXAMPLE 24

A support was prepared by calcining boehmite (2400 g) mixed with cesium fluoride (17.4 g). The finished support contained 360 ppm Si, 202 ppm Cs and 202 ppm Fe. Extraction with dilute sulphuric acid showed the presence of 180 ppm $C_s$. The pore volume was 0.58 mls/g and the BET surface area was 0.75 $M^2/g$. Catalyst 19 was prepared on this support using the methods employed for the preparation of catalyst 3. The resulting catalyst comprised 2058 g atoms of Ag, 4.8 g atoms of Cs, 1.2 g atom of Mo, and 1.2 g atom of S, each per million g catalyst. In tests according to the procedure of example 3, $T_{30}$ was 225° C., $S_{30}$ was 84.6%, and the rate of ethylene oxidation was 4.9 moles/liter hour.

EXAMPLE 25

Catalyst 20 was prepared in the same manner as catalyst 3 excepting that the molybdate, sulphate and cesium solutions were made up such that a volume equivalent to the pore volumes of the catalyst provided 1.0 g atom of molybdenum, 1.5 g atom of sulphur and 4.8 g atoms of cesium per million g of catalyst. To provide a lithium content in catalyst 20, lithium oxalate was included in the impregnating solution: the lithium content of the catalyst 20 was 20 g atoms per million g of catalyst. In test according the procedure of example 3, $T_{30}$ was 223° C., $S_{30}$ was 85.5% and the rate of ethylene oxidation was 4.2 moles/liter hr.

EXAMPLE 26

A support was prepared by calcining extrudates made from a paste comprising boehmite (846 g), fumed silica (54 g), acetic acid (10 mls), concentrated hydrofluoric acid, (46 mls), and water (385 mls). The finished support contained 2.4% Si, 162 ppm Na, 167 ppm Ca and 172 ppm Fe. The pore volume was 1.07 mls/g and the BET surface area was 2.4 $m^2/g$. Catalyst 21 was prepared on this support using the methods employed for the preparation of catalyst 3. The resulting catalyst comprised 2962 g atoms Ag, 10.8 g atoms of Cs, 3.6 g atoms of Mo, and 1.9 g atoms of S, each per million g of catalysts. In tests according to the procedure of example 3, $T_{30}$ was 220° C., $S_{30}$ was 84.8%, and the rate of ethylene oxidation was 4.3 moles/liter/hour.

TABLE 1

| EXAMPLE | SUPPORT | SUPPORT SURFACE AREA, $M^2/G$ | CATALYST | G ATOMS/MILLION G CATALYST | | | |
|---|---|---|---|---|---|---|---|
| | | | | Ag | Cr | S | Cs |
| 1 | A | 0.7 | 1 | 1537 | 0.8 | 1.5 | 5.0 |
| 2 | A | 0.7 | 2 | 1537 | 0.6 | 1.5 | 5.0 |

| EXAMPLE | G ATOMS/$KM^2$ SUPPORT | | | G ATOMS/THOUSAND G ATOMS Ag | | | G ATOMS/G ATOM Cs | | |
|---|---|---|---|---|---|---|---|---|---|
| | Cr | S | Cs | Cr | S | Cs | Cr | S | Cr+S |
| 1 | 1.3 | 2.5 | 8.2 | 0.6 | 1.0 | 3.5 | 0.2 | 0.3 | 0.5 |
| 2 | 0.8 | 2.5 | 8.2 | 0.4 | 1.0 | 3.5 | 0.1 | 0.3 | 0.4 |

| EXAMPLE | G ATOMS Cr/ G ATOM S | $S_{30}$ % | $T_{30}$ °C. | RATE OF ETHYLENE OXIDATION, MOLES/ LITER OF CATALYST BED/HOUR |
|---|---|---|---|---|
| 1 | 0.5 | 85.2 | 239 | 4.2 |
| 2 | 0.4 | 83.8 | 233 | 4.0 |

TABLE 2

| COMPARATIVE EXAMPLES | SUPPORT | SUPPORT SURFACE AREA, $M^2/G$ | CATALYST | G ATOMS/MILLION G CATALYST | | | |
|---|---|---|---|---|---|---|---|
| | | | | Ag | Cr | S | $C_s$ |
| 1 | A | 0.7 | I | 1537 | 0.8 | 0 | 5.0 |
| 2 | A | 0.7 | II | 1537 | 0 | 1.5 | 5.0 |
| 3 | A | 0.7 | III | 1537 | 0.8 | 1.5 | 0 |

| COMPARATIVE EXAMPLES | G ATOMS/$KM^2$ SUPPORT | | | G ATOMS/THOUSAND G ATOMS Ag | | | G ATOMS/G ATOM $C_s$ | | |
|---|---|---|---|---|---|---|---|---|---|
| | Cr | S | $C_s$ | Cr | S | $C_s$ | Cr | S | Cr+S |
| 1 | 1.3 | 0 | 8.2 | 0.6 | 0 | 3.5 | 0.2 | 0 | 0.2 |
| 2 | 0 | 2.5 | 8.2 | 0 | 1.0 | 3.5 | 0 | 0.3 | 0.3 |
| 3 | 1.3 | 2.5 | 0 | 0.6 | 1.0 | 0 | 0.2 | 0.3 | 0.5 |

| COMPARATIVE EXAMPLES | G ATOMS Cr/ G ATOM S | $S_{30}$ % | $T_{30}$ °C. | RATE OF ETHYLENE OXIDATION, MOLES/ LITER OF CATALYST BED/HOUR |
|---|---|---|---|---|
| 1 | — | 79 | 270 | 3.8 |
| 2 | — | 82.7 | 217 | 3.9 |
| 3 | 0.5 | 76 | 227 | 3.7 |

TABLE 3

| SUPPORT SURFACE AREA, | G ATOMS/MILLION G CATALYST | G ATOMS/$KM^2$ SUPPORT | G ATOMS/THOUSAND G ATOMS Ag |
|---|---|---|---|

TABLE 3-continued

| EXAMPLE | SUPPORT | M²/G | CATALYST | Ag | Mo | S | C_s | Mo | S | C_s | Mo | S | C_s |
|---|---|---|---|---|---|---|---|---|---|---|---|---|---|
| 3 | A | 0.7 | 3 | 1435 | 1.3 | 1.4 | 4.8 | 1.8 | 2.0 | 6.9 | 0.9 | 1.0 | 3.4 |
| 4 | A | 0.7 | 4 | 1435 | 0.6 | 1.4 | 4.8 | 0.9 | 2.0 | 6.9 | 0.4 | 1.0 | 3.4 |
| 5 | A | 0.7 | 5 | 1425 | 0.9 | 1.4 | 4.8 | 1.4 | 2.0 | 6.9 | 0.7 | 1.0 | 3.4 |
| 6 | A | 0.7 | 6 | 1450 | 1.6 | 1.4 | 4.8 | 2.2 | 2.0 | 6.9 | 1.1 | 1.0 | 3.3 |
| 7 | A | 0.7 | 7 | 1410 | 1.9 | 1.4 | 4.8 | 2.7 | 2.0 | 6.9 | 1.3 | 1.0 | 3.3 |

| EXAMPLE | G ATOMS/G ATOM $C_s$ | | | G ATOMS Mo/ G ATOM S | $S_{30}$ % | $T_{30}$ °C. | RATE OF ETHYLENE OXIDATION, MOLES/ LITER OF CATALYST BED/HOUR |
|---|---|---|---|---|---|---|---|
| | Mo | S | Mo+S | | | | |
| 3 | 0.3 | 0.3 | 0.6 | 0.9 | 85.5 | 231 | 4.2 |
| 4 | 0.1 | 0.3 | 0.4 | 0.4 | 84.2 | 218 | 4.0 |
| 5 | 0.2 | 0.3 | 0.5 | 0.7 | 84.7 | 231 | 4.1 |
| 6 | 0.3 | 0.3 | 0.6 | 1.1 | 83.6 | 238 | 4.0 |
| 7 | 0.4 | 0.3 | 0.7 | 1.3 | 85.0 | 247 | 4.1 |

TABLE 4

| EXAMPLE | SUPPORT | SUPPORT SURFACE AREA, M²/G | CATALYST | G ATOMS/MILLION G CATALYST | | | | G ATOMS/KM² SUPPORT | | | G ATOMS/THOUSAND G ATOMS Ag | | |
|---|---|---|---|---|---|---|---|---|---|---|---|---|---|
| | | | | Ag | Mo | S | C_s | Mo | S | C_s | Mo | S | C_s |
| 8 | A | 0.7 | 3 | 1435 | 1.3 | 1.4 | 4.8 | 1.8 | 2.0 | 6.9 | 0.9 | 1.0 | 3.4 |
| 9 | A | 0.7 | 8 | 1435 | 1.3 | 1.0 | 4.8 | 1.8 | 1.4 | 6.9 | 0.9 | 0.7 | 3.4 |
| 10 | A | 0.7 | 9 | 1435 | 1.3 | 1.4 | 4.8 | 1.8 | 2.0 | 6.9 | 0.9 | 1.0 | 3.4 |
| 11 | A | 0.7 | 10 | 1460 | 1.3 | 2.6 | 4.8 | 1.8 | 3.7 | 6.9 | 0.9 | 1.8 | 3.4 |
| 12 | A | 0.7 | 11 | 1455 | 1.3 | 3.9 | 4.8 | 1.8 | 5.6 | 6.9 | 0.9 | 2.7 | 3.4 |
| 13 | B | 0.6 | 12 | 1400 | 1.8 | 0.9 | 4.6 | 2.8 | 1.4 | 7.1 | 1.3 | 0.6 | 3.3 |

| EXAMPLE | G ATOMS/G ATOM $C_s$ | | | G ATOMS Mo/ G ATOM S | $S_{30}$ % | $T_{30}$ °C. | RATE OF ETHYLENE OXIDATION, MOLES/ LITER OF CATALYST BED/HOUR |
|---|---|---|---|---|---|---|---|
| | Mo | S | Mo+S | | | | |
| 8 | 0.3 | 0.3 | 0.6 | 0.9 | 87.0 | 245 | 8.7 |
| 9 | 0.3 | 0.2 | 0.5 | 1.3 | 84.0 | 231 | 4.0 |
| 10 | 0.3 | 0.3 | 0.6 | 0.9 | 85.5 | 231 | 4.2 |
| 11 | 0.3 | 0.5 | 0.8 | 0.7 | 83.5 | 249 | 4.0 |
| 12 | 0.3 | 0.8 | 1.1 | 0.3 | 83.0 | 270 | 3.9 |
| 13 | 0.4 | 0.2 | 0.6 | 2 | 84.0 | 238 | 4.0 |

TABLE 5

| EXAMPLE | SUPPORT | SUPPORT SURFACE AREA, M²/G | CATALYST | G ATOMS/MILLION G CATALYST | | | |
|---|---|---|---|---|---|---|---|
| | | | | Ag | Mo | S | C_s |
| 14 | A | 0.7 | 3 | 1435 | 1.3 | 1.4 | 4.8 |
| 15 | A | 0.7 | 5 | 1425 | 0.9 | 1.4 | 4.8 |

| EXAMPLE | G ATOMS/KM² SUPPORT | | | G ATOMS/THOUSAND G ATOMS Ag | | | G ATOMS/G ATOM Cs | | |
|---|---|---|---|---|---|---|---|---|---|
| | Mo | S | C_s | Mo | S | C_s | Mo | S | Mo+S |
| 14 | 1.8 | 2.0 | 6.9 | 0.9 | 1.0 | 3.4 | 0.3 | 0.3 | 0.6 |
| 15 | 1.4 | 2.0 | 6.9 | 0.7 | 1.0 | 3.4 | 0.2 | 0.3 | 0.5 |

| EXAMPLE | G ATOMS Mo/ G ATOM S | $S_{30}$ % | $T_{30}$ °C. | RATE OF ETHYLENE OXIDATION, MOLES/ LITER OF CATALYST BED/HOUR |
|---|---|---|---|---|
| 14 | 0.9 | 86.5 | 252 | 4.3 |
| 15 | 0.7 | 84.1 | 242 | 4.0 |

TABLE 6

| COMPARATIVE EXAMPLES | SUPPORT | SUPPORT SURFACE AREA, M²/G | CATALYST | G ATOMS/MILLION G CATALYST | | | | G ATOMS/KM² SUPPORT | | |
|---|---|---|---|---|---|---|---|---|---|---|
| | | | | Ag | Mo | S | C_s | Mo | S | C_s |
| 4 | A | 0.7 | IV | 1435 | 0 | 0 | 4.8 | 0 | 0 | 6.9 |
| 5 | A | 0.7 | V | 1450 | 0 | 1.4 | 0 | 0 | 2.0 | 0 |
| 6 | A | 0.7 | VI | 1410 | 1.3 | 0 | 0 | 1.8 | 0 | 0 |
| 7 | A | 0.7 | VII | 1420 | 1.3 | 1.4 | 0 | 1.8 | 2.0 | 0 |
| 8 | A | 0.7 | VIII | 1435 | 1.3 | 0 | 4.8 | 1.8 | 0 | 6.9 |
| 9 | A | 0.7 | IX | 1420 | 0 | 1.0 | 4.8 | 0 | 1.4 | 6.9 |
| 10 | A | 0.7 | X | 1450 | 0 | 1.4 | 4.8 | 0 | 2.0 | 6.9 |
| 11 | A | 0.7 | XI | 1410 | 0 | 2.6 | 4.8 | 0 | 3.7 | 6.9 |

| COMPARATIVE | G ATOMS/THOUSAND G ATOMS Ag | G ATOMS/G ATOM C_s | G ATOMS Mo/G | $S_{30}$ | $T_{30}$ | RATE OF ETHYLENE OXIDATION, MOLES/ LITER OF CATALYST |

TABLE 6-continued

| EXAMPLES | Mo | S | $C_s$ | Mo | S | Mo-S | ATOM S | % | °C. | BED/HOUR |
|---|---|---|---|---|---|---|---|---|---|---|
| 4 | 0 | 0 | 3.4 | 0 | 0 | 0 | — | 80.1 | 201 | 3.6 |
| 5 | 0 | 1.0 | 0 | 0 | — | — | — | 76.0 | 213 | 3.7 |
| 6 | 0.9 | 0 | 0 | — | 0 | — | — | 75.1 | 212 | 3.6 |
| 7 | 0.9 | 1.0 | 0 | — | — | — | 0.9 | 75.9 | 227 | 3.7 |
| 8 | 0.9 | 0 | 3.4 | 0.3 | 0 | 0.3 | — | 82.0 | 248 | 3.8 |
| 9 | 0 | 0.7 | 3.4 | 0 | 0.2 | 0.2 | — | 81.7 | 204 | 3.8 |
| 10 | 0 | 1.0 | 3.4 | 0 | 0.3 | 0.3 | — | 82.3 | 200 | 3.8 |
| 11 | 0 | 1.8 | 3.3 | 0 | 0.5 | 0.5 | — | 82.5 | 204 | 3.9 |

TABLE 7

| EXAMPLE | SUPPORT | SUPPORT SURFACE AREA, $M^2/G$ | CATALYST | G ATOMS/MILLION G CATALYST | | | | G ATOMS/KM² SUPPORT | | | G ATOMS/THOUSAND G ATOMS Ag | | |
|---|---|---|---|---|---|---|---|---|---|---|---|---|---|
| | | | | Ag | W | S | $C_s$ | W | S | $C_s$ | W | S | $C_s$ |
| 18 | A | 0.7 | 15 | 1405 | 1.7 | 1.4 | 5.1 | 2.4 | 2.0 | 7.3 | 1.2 | 1.0 | 3.6 |
| 19 | A | 0.7 | 16 | 1435 | 1.4 | 1.4 | 5.5 | 2.0 | 2.0 | 7.9 | 1.0 | 1.0 | 3.8 |
| 20 | A | 0.7 | 17 | 1450 | 1.4 | 1.4 | 5.1 | 2.0 | 2.0 | 7.3 | 1.0 | 1.0 | 3.5 |
| 21 | A | 0.7 | 15 | 1405 | 1.7 | 1.4 | 5.1 | 2.4 | 2.0 | 7.3 | 1.2 | 1.0 | 3.6 |
| 22 | A | 0.7 | 16 | 1435 | 1.4 | 1.4 | 5.5 | 2.0 | 2.0 | 7.9 | 1.0 | 1.0 | 3.8 |

| EXAMPLE | G ATOMS/G ATOM $C_s$ | | | G ATOMS W/ G ATOM S | $S_{30}$ % | $T_{30}$ °C. | RATE OF ETHYLENE OXIDATION, MOLES/ LITER OF CATALYST BED/HOUR |
|---|---|---|---|---|---|---|---|
| | W | S | W-S | | | | |
| 18 | 0.3 | 0.3 | 0.6 | 1.2 | 84.3 | 230 | 4.0 |
| 19 | 0.3 | 0.3 | 0.6 | 1.0 | 84.0 | 231 | 4.0 |
| 20 | 0.3 | 0.3 | 0.6 | 1.0 | 83.8 | 225 | 4.0 |
| 21 | 0.3 | 0.3 | 0.6 | 1.2 | 84.4 | 234 | 4.0 |
| 22 | 0.3 | 0.3 | 0.6 | 1.0 | 85.6 | 239 | 4.2 |

We claim:

1. A process for producing ethylene oxide which comprises contacting ethylene and oxygen in the presence of a reaction modifier selected from chlorine-substituted $C_{1-6}$ hydrocarbons, with a catalyst which comprises silver supported on a porous heat resisting support, a group VI A transition metal, namely chromium, molybdenum and/or tungsten, an alkali metal selected from potassium, rubidium and cesium and sulphur which catalyst is free from rhenium.

2. A process of producing ethylene oxide which comprises contacting ethylene and oxygen in the presence of a reaction modifier selected from chlorine-substituted $C_{1-6}$ hydrocarbons with a catalyst which consists of silver supported on a porous heat resisting support, a group VI A transition metal selected from the group consisting of chromium, molybdenum, and tungsten, an alkali metal selected from potassium, rubidium and cesium, and sulphur, said catalyst including 3 to 50% by weight of silver and 0.1 to 5 gram atoms of the transition metal, 0.1 to 10 gram atoms of sulphur and 0.1 to 15 gram atoms of the alkali metal per million grams of catalyst.

3. A process as claimed in claim 1 in which the sulphur is present as sulphate ions and in which the porous, heat resisting support is alumina.

4. A process as claimed in claim 2 in which the sulphur is present as sulphate ions and in which the porous, heat resisting support is α-alumina.

* * * * *